(12) United States Patent
Engmark et al.

(10) Patent No.: US 9,675,808 B2
(45) Date of Patent: Jun. 13, 2017

(54) BATTERY AND CAPACITOR ARRANGEMENT FOR AN IMPLANTABLE MEDICAL DEVICE

(75) Inventors: David B. Engmark, Bethel, MN (US); Andrew J. Ries, Lino Lakes, MN (US); Todd H. Schaefer, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 245 days.

(21) Appl. No.: 13/246,613

(22) Filed: Sep. 27, 2011

(65) Prior Publication Data

US 2013/0079600 A1 Mar. 28, 2013

(51) Int. Cl.
*A61N 1/375* (2006.01)

(52) U.S. Cl.
CPC .................. *A61N 1/3758* (2013.01)

(58) Field of Classification Search
CPC .................................... A61N 1/3758
USPC ............................................ 607/36
See application file for complete search history.

(56) References Cited

U.S. PATENT DOCUMENTS

| | | | |
|---|---|---|---|
| 2,936,514 A | 5/1960 | Millard | |
| 4,831,494 A | 5/1989 | Arnold et al. | |
| 5,131,388 A | 7/1992 | Pless | |
| 5,749,910 A | 5/1998 | Brumwell | |
| 6,219,222 B1 | 4/2001 | Shah et al. | |
| 6,243,605 B1 | 6/2001 | Youker et al. | |
| 6,283,985 B1 | 9/2001 | Harguth et al. | |
| 6,706,059 B2 | 3/2004 | Harguth et al. | |
| 6,721,602 B2 | 4/2004 | Engmark et al. | |
| 6,761,728 B2 | 7/2004 | Harguth et al. | |
| 7,016,175 B2 | 3/2006 | MacNeal et al. | |
| 7,023,688 B2 | 4/2006 | Kazama | |
| D523,144 S | 6/2006 | Wenger et al. | |
| 7,131,988 B2 | 11/2006 | Harguth et al. | |
| 7,170,737 B2 | 1/2007 | MacNeal et al. | |
| 7,171,267 B2 | 1/2007 | Harguth et al. | |
| 7,544,563 B2 | 6/2009 | Manning | |
| 7,557,015 B2 | 7/2009 | Sandhu et al. | |
| 7,803,014 B2 | 9/2010 | Sprain et al. | |
| 2003/0204216 A1* | 10/2003 | Ries et al. | 607/36 |

(Continued)

OTHER PUBLICATIONS

Reed, "Characterization of Tantalum Polymer Capacitors," NEPP Task 1.21.5, Phase 1, FY05, 26 pages.

(Continued)

*Primary Examiner* — Eric D. Bertram

(57) ABSTRACT

An implantable medical device includes a housing forming an internal cavity, the housing defining a profile with a height and a width and further defining a thickness perpendicular to its profile. The thickness of the housing is shorter than both the height and the width of the profile of the housing. The implantable medical device further includes at least one battery within the internal cavity, at least one capacitor adjacent the battery within the internal cavity, the capacitor and the battery being located along a common plane within the internal cavity, and circuitry within the internal cavity. The circuitry extends over both the battery and the capacitor within the internal cavity such that the circuitry is in a stacked arrangement relative to the battery and the capacitor.

17 Claims, 9 Drawing Sheets

(56) References Cited

U.S. PATENT DOCUMENTS

2005/0154423 A1* 7/2005 Goedeke et al. ............... 607/36
2009/0266573 A1* 10/2009 Engmark ............... A61N 1/375
174/50.54

OTHER PUBLICATIONS

P0039829WOU2 (PCT/US2012/056991) PCT Notification of Transmittal of the International Search Report and the Written Opinion of the International Searching Authority.

* cited by examiner

BATTERY AND CAPACITOR ARRANGEMENT FOR AN IMPLANTABLE MEDICAL DEVICE

TECHNICAL FIELD

The disclosure relates to implantable medical devices.

BACKGROUND

A wide variety of implantable medical devices that deliver a therapy or monitor a physiologic condition of a patient have been clinically implanted or proposed for clinical implantation in patients. Some implantable medical devices may employ one or more elongated electrical leads and/or sensors. Such implantable medical devices may deliver therapy or monitor the heart, muscle, nerve, brain, stomach or other organs. In some cases, implantable medical devices deliver electrical stimulation therapy and/or monitor physiological signals via one or more electrodes or sensor elements, at least some of which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead. A proximal portion of the lead may be coupled to an implantable medical device housing, which may contain electronic circuitry such as stimulation generation and/or sensing circuitry. In some cases, electrodes or sensors may be positioned on an implantable medical device (IMD) housing as an alternative or in addition to electrodes or sensors deployed on one or more leads.

Implantable cardiac devices, such as cardiac pacemakers or implantable cardioverter defibrillators, provide therapeutic electrical stimulation to the heart by delivering electrical therapy signals such as pulses or shocks for pacing, cardioversion, or defibrillation via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an implantable medical device may deliver pacing, cardioversion or defibrillation signals to the heart of the patient upon detecting ventricular tachycardia, and deliver defibrillation therapy to a patient's heart upon detecting ventricular fibrillation.

SUMMARY

In general, the disclosure is directed to the design and arrangement of components within a housing of an implantable medical device. In one example, an implantable medical device includes at least one battery and at least one capacitor adjacent one another in a first plane and circuitry for the IMD, such as a hybrid integrated circuit in a stacked arrangement with the at least one battery and the at least one capacitor of the IMD.

In one example, this disclosure is directed to an implantable medical device comprising a housing forming an internal cavity, the housing defining a profile with a height and a width and further defining a thickness perpendicular to its profile. The thickness of the housing is shorter than both the height and the width of the profile of the housing. The implantable medical device further comprises at least one battery within the internal cavity, at least one capacitor adjacent the battery within the internal cavity, the capacitor and the battery being located along a common plane within the internal cavity, and circuitry within the internal cavity. The circuitry extends over both the battery and the capacitor within the internal cavity such that the circuitry is in a stacked arrangement relative to the battery and the capacitor.

In another example, this disclosure is directed to a system comprising an implantable medical device and a medical lead. The implantable medical device includes a housing forming an internal cavity, the housing defining a profile with a height and a width and further defining a thickness perpendicular to its profile, wherein the thickness of the housing is shorter than both the height and the width of the profile of the housing, at least one battery within the internal cavity, at least one capacitor adjacent the battery within the internal cavity, the capacitor and the battery being located along a common plane within the internal cavity, circuitry within the internal cavity. The circuitry extends over both the battery and the capacitor within the internal cavity such that the circuitry is in a stacked arrangement relative to the battery and the capacitor. The implantable medical device further includes a header assembly external to the housing, the header assembly being in electrical contact with the circuitry within the internal cavity. The at least one medical lead is in mechanical and electrical contact with the implantable medical device via the header assembly.

In another example, this disclosure is directed to a method comprising generating an electrical stimulation therapy for delivery to a patient with an implantable medical device implanted within the patient. The implantable medical device includes a housing forming an internal cavity, the housing defining a profile with a height and a width and further defining a thickness perpendicular to its profile. The thickness of the housing is shorter than both the height and the width of the profile of the housing. The implantable medical device further includes at least one battery within the internal cavity, at least one capacitor adjacent the battery within the internal cavity, the capacitor and the battery being located along a common plane within the internal cavity, and circuitry within the internal cavity. The circuitry extends over both the battery and the capacitor within the internal cavity such that the circuitry is in a stacked arrangement relative to the battery and the capacitor.

The details of one or more examples are set forth in the accompanying drawings and the description below. Other features, objects, and advantages of the disclosure will be apparent from the description and drawings, and from the claims.

DETAILED DESCRIPTION

Figure 1:
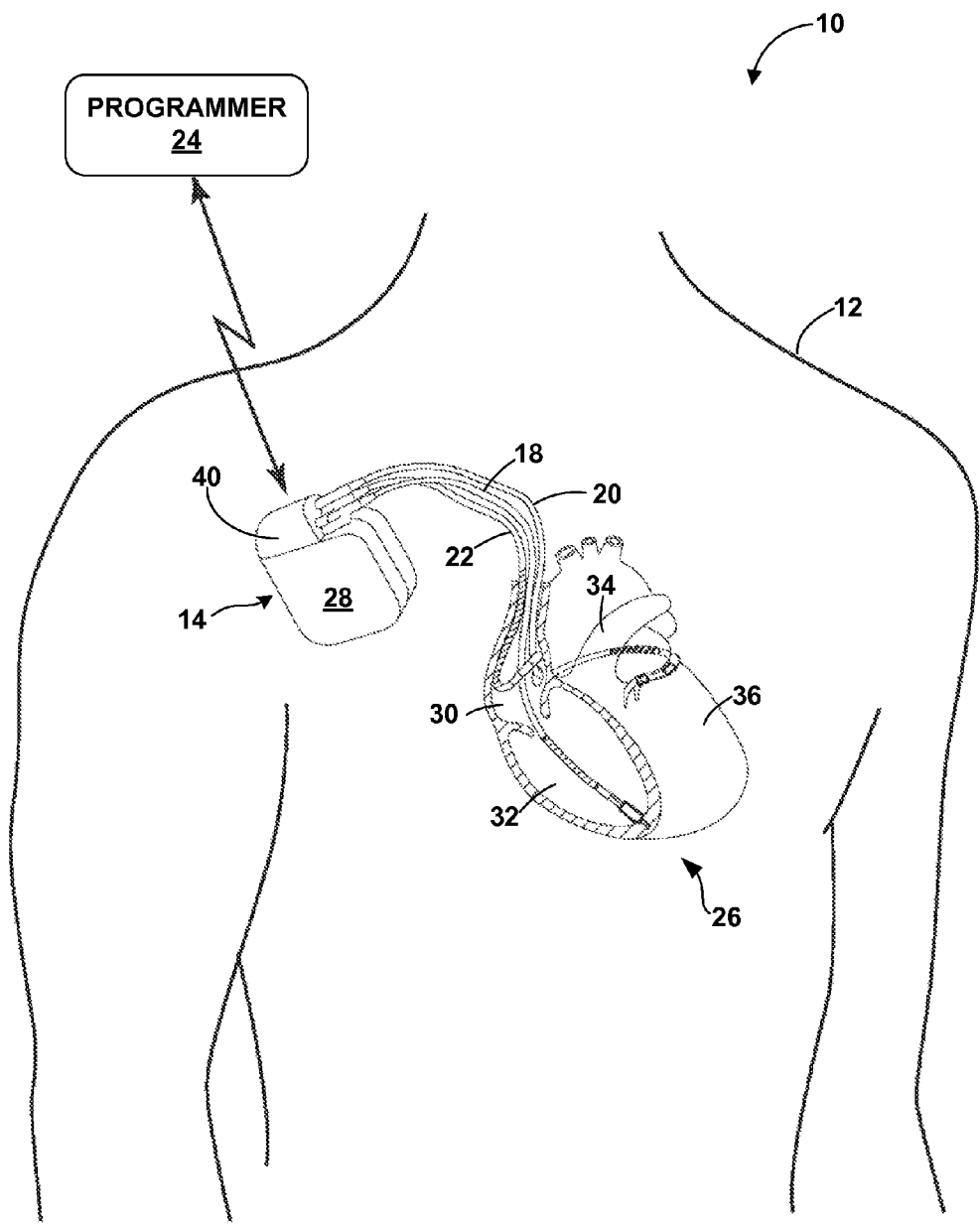
FIG. 1 is a conceptual diagram illustrating an example system that includes an implantable medical device (IMD) configured to deliver electrical stimulation to and/or monitor a patient.

FIG. 1 is a conceptual diagram illustrating an example system 10 that provides therapy to and/or monitors patient 12. System 10 includes implantable medical device (IMD) 14 and leads 18, 20, 22, and programmer 24. Leads 18, 20, 22 are mechanically and electrically coupled to IMD 14 via a header assembly, which may be connected housing 28 of IMD 14 as shown in FIG. 1. In the example of FIG. 1, the header assembly comprises a lead connector assembly 40 that connects to leads 18, 20, 22 to IMD 14. Housing 28 and lead connector assembly 40 are separate components that are mechanically coupled together, e.g., via bracket and pin connections or snap-on connections. As discussed in further detail below, IMD 14 includes at least one battery and at least one capacitor adjacent one another in a first plane and circuitry for the IMD, such as a hybrid integrated circuit, in an adjacent plane parallel to the first plane. In this manner, in contrast to some previous IMD designs, the circuitry extends over both the battery and the capacitors instead of extending over only the battery.

In the example shown in FIG. 1, housing 28 and lead connector assembly 40 can be fabricated from any suitable biocompatible material or combination of biocompatible materials, such as, but not limited to, stainless steel or titanium. Housing 28 and lead connector assembly 40 may be formed from the same material or materials, or different materials.

In some examples, IMD 14 generates and delivers electrical stimulation to heart 26 via electrodes carried by one or more of leads 18, 20, 22 in order to manage a cardiac rhythm of heart 26. In such examples, IMD 14 includes a therapy module that generates at least one of pacing, cardioversion, defibrillation or cardiac resynchronization therapy. The pacing therapy may include, for example, antitachyarrhythmia pacing (ATP) and pacing therapies designed to prevent ventricular tachycardia, ventricular fibrillation, atrial tachycardia, and/or atrial fibrillation, or cardiac resynchronization therapy (CRT). In some examples, IMD 14 provides pacing, but not cardioversion or defibrillation, while in other examples, IMD 14 provides cardioversion or defibrillation, but not pacing. In addition, in further examples, IMD 14 provides pacing, cardioversion, and defibrillation. Alternatively, or in addition to, the therapy module, IMD 14 may include a sensing module. The sensing module may sense one or more physiological conditions of a patient such as electrical depolarization/repolarization signals from heart 26 (referred to as "electrogram" or EGM), intracardiac or intravascular pressure, activity, posture, respiration, or thoracic impedance. In other examples, an IMD may include more or less than three leads for delivering therapy and or sensing.

In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 26. Right atrial (RA) lead 22 extends through one or more veins and the vena cava, and into the right atrium 30 of heart 26. In other examples, IMD 14 delivers stimulation therapy to heart 26 by delivering stimulation to an extravascular tissue site in addition to or instead of delivering stimulation via electrodes of intravascular leads 18, 20, 22. An extravascular tissue site is outside of heart 26 and outside of arteries, veins, or other vasculature of patient 12.

IMD 14 may sense electrical signals attendant to the depolarization and repolarization of heart 26 via electrodes (not shown in FIG. 1) coupled to at least one of the leads 18, 20, 22. In some examples, IMD 14 provides pacing pulses to heart 26 based on the electrical signals sensed within heart 26. The configurations of electrodes used by IMD 14 for sensing and pacing may be unipolar or bipolar. IMD 14 may also provide defibrillation therapy and/or cardioversion therapy via electrodes located on at least one of the leads 18, 20, 22. IMD 14 may detect arrhythmia of heart 26, such as fibrillation of ventricles 32 and 36, and IMD 14 may be programmed to deliver a progression of therapies, e.g., pulses with increasing energy levels, until a fibrillation of heart 26 is stopped. IMD 14 may detect fibrillation employing one or more fibrillation detection techniques known in the art.

In some examples, IMD 14 may also be referred to as a signal generator, stimulation generator or an electrical stimulator. In some examples, lead 16 may also carry one or more sense electrodes to permit IMD 14 to sense electrical signals within patient 12. In some examples, the same electrodes may be used for sensing and for stimulation.

In the example of FIG. 1, IMD 14 has been implanted in patient 12 at a location that allows leads 18, 20, 22 to be positioned within heart 26. For example, IMD 14 may be subcutaneously or submuscularly implanted in the body of a patient 12 (e.g., in a chest cavity, lower back, lower abdomen, or buttocks of patient 12).

In the example shown in FIG. 1, IMD 14 provides cardiac rhythm therapy. Accordingly, the components for generating and delivering the pacing, cardioversion and/or defibrillation therapy via leads 18, 20, and 22 may be substantially contained within outer housing 28 of IMD 14. Lead connector assembly 40 includes electrical connectors that respectively mechanically couple leads 18, 20, 22 to IMD 14 and electrically connect leads 18, 20, 22 to a therapy or sensing module within housing 28. For example, a proximal end of each of leads 16, 18, 20, may be both electrically and mechanically coupled to lead connector assembly 40 of IMD 14 either directly or indirectly (e.g., via a lead extension). Electrical conductors disposed in the respective lead body may electrically connect stimulation electrodes (and sense electrodes, if present) of leads 18, 20, 22 to the therapy and/or sensing modules within IMD 14 via lead connector assembly 40. Lead connector assembly 40 may also be referred to as a header assembly or a connector block.

While the disclosure primarily describes leads as being directly connected to lead connector assembly 40, in other examples, leads, such as leads 18, 20, 22, may be indirectly mechanically and electrically connected to lead connector assembly 40 via one or more lead extensions. A lead extension may effectively elongate a lead. In addition, in some examples, a bifurcated or trifurcated lead extension may be useful for mechanically and electrically connecting more than one lead to a common electrical connector of lead connector assembly 40.

In some examples, IMD 14 also includes one or more housing electrodes, which may be formed integrally with an outer surface of hermetically-sealed housing 28 of IMD 14 or otherwise coupled to housing 28. In some examples, the housing electrode may be defined by an uninsulated portion of an outward facing portion of housing 28. Other divisions between insulated and uninsulated portions of housing 28 may be employed to define two or more housing electrodes. In some examples, such as the example shown in FIG. 1, the housing electrode may comprise substantially all of housing 28. In other examples, one or more electrodes may be embedded into an insulating casing that surrounds the outer surface of housing 28 or otherwise attached to outer housing 28 of IMD 14. Any of the electrodes of leads 18, 20, 22 may be used for unipolar sensing or stimulation in combination with the one or more housing electrodes.

In some examples, IMD 14 includes one or more header assembly electrodes in addition to or instead of electrodes of leads 18, 20 and 22. The header assembly electrodes may be formed integrally with an outer surface of the header assembly, such as the outer surface of lead connector assembly 40 of IMD 14. In some examples, the header assembly electrode may be defined by an uninsulated portion of an outward facing portion of the header assembly. Other divisions between insulated and uninsulated portions of the header assembly may be employed to define two or more header assembly electrodes. In some examples, such as the example shown in FIG. 1, the header assembly electrode may comprise substantially all of lead connector 40. In other examples, one or more electrodes may be embedded into an insulating casing that surrounds the outer surface of lead connector 40 or otherwise attached to lead connector 40. In further examples, the header assembly may not connect to any leads. In this case, a plurality of header assembly electrodes, housing electrodes or both may be used to monitor one or more parameters of patient 12. The header assembly may also include one or more feedthroughs via which other conductive components (e.g., antenna) within the header assembly couple to electronic components within housing 28 of IMD 14 (e.g., transceiver).

As shown in FIG. 1, system 10 also includes programmer 24. In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with IMD 14. For example, the user may interact with programmer 24 to retrieve physiological or diagnostic information from IMD 14. A user may also interact with programmer 24 to program IMD 14, e.g., select values for operational parameters for one or more of the stimulation therapies delivered by IMD 14. For example, the user may use programmer 24 to retrieve information from IMD 14 regarding the rhythm of heart 26, trends therein over time, or tachyarrhythmia episodes. As another example, the user may use programmer 24 to retrieve information from IMD 14 regarding other sensed physiological parameters of patient 12, such as electrical depolarization/repolarization signals from heart 26 (referred to as "electrogram" or EGM), intracardiac or intravascular pressure, activity, posture, respiration, or thoracic impedance. As another example, the user may use programmer 24 to retrieve information from IMD 14 regarding the performance or integrity of IMD 14 or other components of system 10 corresponding to the first stimulation therapy, such as leads 18, 20, and 22, or a power source of IMD 14.

The user may use programmer 24 to program a therapy progression, select electrodes used to deliver defibrillation pulses, select waveforms for the defibrillation pulse, or select or configure a fibrillation detection algorithm for IMD 14. The user may also use programmer 24 to program aspects of other therapies provided by IMD 14, such as cardioversion, pacing or other electrical stimulation therapies. For example, with the aid of programmer 24, a user may select therapy parameters for the pacing, cardioversion, and/or defibrillation therapy delivered by leads 18, 20, 22.

Programmer 24 may communicate with IMD 14 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 14 implant site in order to improve the quality or security of communication between IMD 14 and programmer 24.

Figure 2:
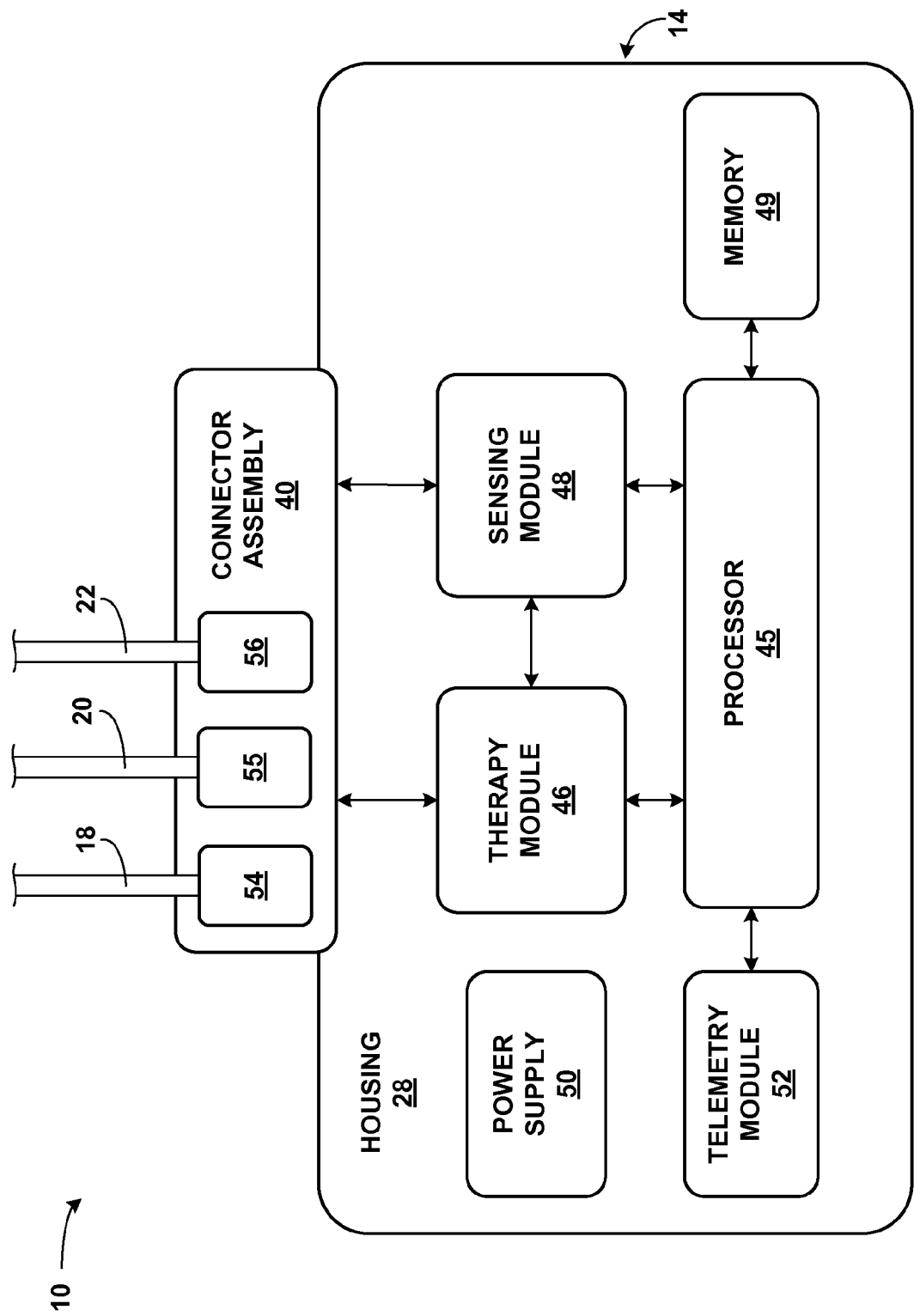
FIG. 2 is a functional block diagram illustrating the IMD of FIG. 1.

FIG. 2 is a functional block diagram illustrating example system 10 including IMD 14, lead connector assembly 40 and leads 18, 20, 22. As shown in FIG. 2, IMD 14 includes processor 45, therapy module 46, sensing module 48, memory 49, power supply 50, and telemetry module 52. Memory 49 may include computer-readable instructions that, when executed by processor 45, cause processor 45 to perform various functions attributed to processor herein. Memory 49 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 45 may include any one or more of a microprocessor, a controller, a digital signal processor (DSP), an application specific integrated circuit (ASIC), a field-programmable gate array (FPGA), or equivalent discrete or integrated logic circuitry. In some examples, processor 45 may include multiple components, such as any combination of one or more microprocessors, one or more controllers, one or more DSPs, one or more ASICs, or one or more FPGAs, as well as other discrete or integrated logic circuitry. The functions attributed to processor 45 herein may be embodied as software, firmware, hardware or any combination thereof. Processor 45 may control modules 46, 48, respectively, to generate and deliver therapy to patient 12 and/or sense one or more physiological conditions of a patient according to one or more control programs, which may be stored in memory 49.

Therapy module 46 includes a signal generator to generate the stimulation signals for delivery to patient 12. Therapy module 46 may be configured generate and deliver electrical stimulation signals including at least one of pacing, cardioversion or defibrillation therapy to heart 26 of patient 12 via leads 18, 20, 22. If therapy module 46 is configured to generate and deliver defibrillation pulses to heart 26, therapy module 46 may include a high voltage charge circuit and a high voltage output circuit. If therapy module 46 is configured to generate and deliver pacing pulses to heart 26, processor 45 may include pacer timing and control module, which may be embodied as hardware, firmware, software, or any combination thereof. The pacer timing and control module may comprise a dedicated hardware circuit, such as an ASIC, separate from other processor 45 components, such as a microprocessor, or a software module executed by a component of processor 45, which may be a microprocessor or ASIC. The pacer timing and control module may be used by processor 45 to time the delivery of pacing pulses to heart 26.

Sensing module 48 monitors signals from at least one of the electrodes of leads 18, 20, 22, the header assembly and/or housing 28 in order to monitor electrical activity of heart 26, e.g., via an EGM signal. In some examples, sensing module 48 may include one or more sensing channels, each of which may comprise an amplifier. Under the control of processor 45, the switch module of sensing module 48 may couple the outputs from the selected electrodes to one of the sensing channels. The sensed electrical activity of heart 26 may be used to control the timing of the delivery of pacing, cardioversion or defibrillation shocks by therapy module 46. For example, processor 45 may employ any suitable arrhythmia detection methodologies in order to detect an arrhythmia based on electrical cardiac signals sensed by sensing module 48, and the detection of an arrhythmia may be used to control the delivery of defibrillation shocks by therapy module 46, e.g., to attempt to terminate the detected arrhythmia.

Modules 46, 48 may be electrically coupled to one or more electrodes of the respective lead 18, 20 and 22 via conductors of the respective lead, or, in the case of a housing electrode, via an electrical conductor disposed within housing 28 of IMD 14. In some examples, therapy module 46 may deliver defibrillation shocks to heart 26 via at least two electrodes coupled to leads 18, 20, 22, connector assembly 40 or housing 28. Therapy module 46 may deliver pacing pulses via the housing electrode, ring electrodes coupled to leads 18, 20, 22, respectively, and/or helical electrodes of leads 18, 20, 22. In some examples, therapy module 46 may deliver pacing, cardioversion, or defibrillation stimulation in the form of electrical pulses.

Module 46, 48 may include a switch module, and processor 45 may use the switch module to select, e.g., via a data/address bus, which of the available electrodes of housing 28 and leads 16, 42 are used to deliver electrical stimulation. The switch module may include a switch array, switch matrix, multiplexer, or any other type of switching device suitable to selectively couple stimulation energy to selected electrodes. In other examples, however, module 46, 48 may independently deliver stimulation and/or sense via the electrodes without a switch matrix.

In some examples modules 46, 48 may share one or more components that operate for each of the modules as described herein. For example, in some cases, therapy module 46 and sensing module 48 may share a switch module. In addition, in some examples, modules 46, 48 may include components dedicated to only a single module. For example, modules 46, 48 may have respective processors and/or memories.

Telemetry module 52 includes any suitable hardware, firmware, software or any combination thereof for communicating with another device, such as programmer 24 (FIG. 1). Under control of processor 45 of IMD 14, telemetry module 52 may receive downlink telemetry from and send uplink telemetry to programmer 24 with the aid of an antenna, which may be internal and/or external. IMD 14 may provide the data to be uplinked to programmer 24 and the control signals for the telemetry circuit within telemetry module 52 e.g., via an address/data bus. In some examples, telemetry module 52 may provide received data to a processor of IMD 14 via a multiplexer.

The various components of IMD 14 may be coupled to power supply 50, which may include a rechargeable or non-rechargeable battery. A non-rechargeable battery may be selected to last for several years, while a rechargeable battery may be inductively charged from an external device, e.g., on a daily or weekly basis. In other examples, power supply 50 may be powered by proximal inductive interaction with an external power supply carried by patient 12. In the example of IMD 100, discussed below with respect to FIGS. 3A-3E, a power supply such as power supply 50 may include a battery comprising electrochemical cells and further include one or more capacitors.

As previously described, IMD 14 may be mechanically coupled to leads 18, 20 and 22, and electrically coupled to electrodes of leads 18, 20 and 22 via lead connector assembly 40. Although FIG. 2 illustrates a lead connector assembly configured to receive three leads, in other examples, lead connector modules or assemblies described herein may include any suitable number of electrical connectors to electrically couple any suitable number of leads to therapy module 46 and sensing module 48. Accordingly, in some examples, lead connector assembly 40 may include additional electrical connectors that are configured to receive additional leads of system 10.

Electrical connectors 54, 55, 56 within connection assembly 40 may be any suitable type of electrical connector capable of electrically and mechanically coupling leads 18, 20 and 22, respectively, to IMD 14. For example, electrical connectors 54, 55, 56 may each be configured as receptacles configured to receive a proximal end of the respective leads 18, 20, 22 (or a lead extension). In some examples, the proximal end of a lead (or lead extension) may be physically secured in the corresponding electrical connector receptacle via a set screw, while in other examples, the proximal end of each lead (or lead extension) may mate with the receptacle in a self-securing manner. In some examples, connectors 54, 55, 56 are Bayonet Neill Concelman (BNC) electrical connectors or have configurations similar to BNC electrical connectors, which are physically configured to mate with the respective leads 18, 20, 22, 16. In addition, in some examples, connectors 54, 55, 56 are Treaded Neill Concelman (TNC) type electrical connectors or have configurations (e.g., bayonet mount style) similar to TNC electrical connectors, which are configured to physically mate with and receive leads 18, 20 and 22 in a threaded configuration. In other examples, connectors 54, 55, 56 are connected to leads 42, 16 without the aid of a set screw, such as with the aid of a lever that pushes leads 18, 20 and 22 into physical and electrical connection with electrical contacts within the respective electrical connectors 54, 55, 56.

Figure 3A:
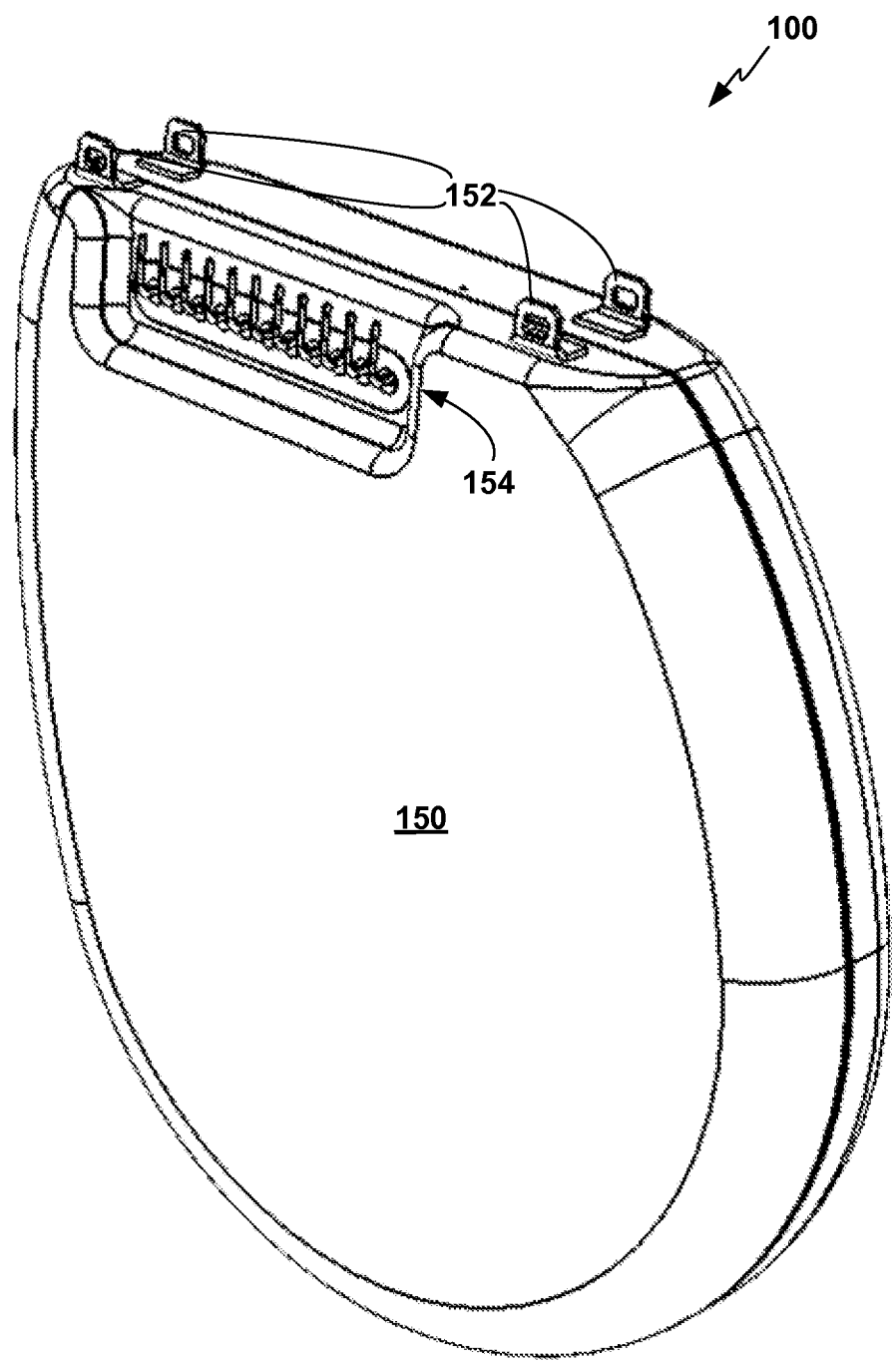
FIGS. 3A-3E illustrate an example IMD with circuitry that extends over both a battery and a capacitor within an internal cavity of the IMD housing such that the circuitry is in a stacked arrangement relative to the battery and the capacitor.
Figure 3B:
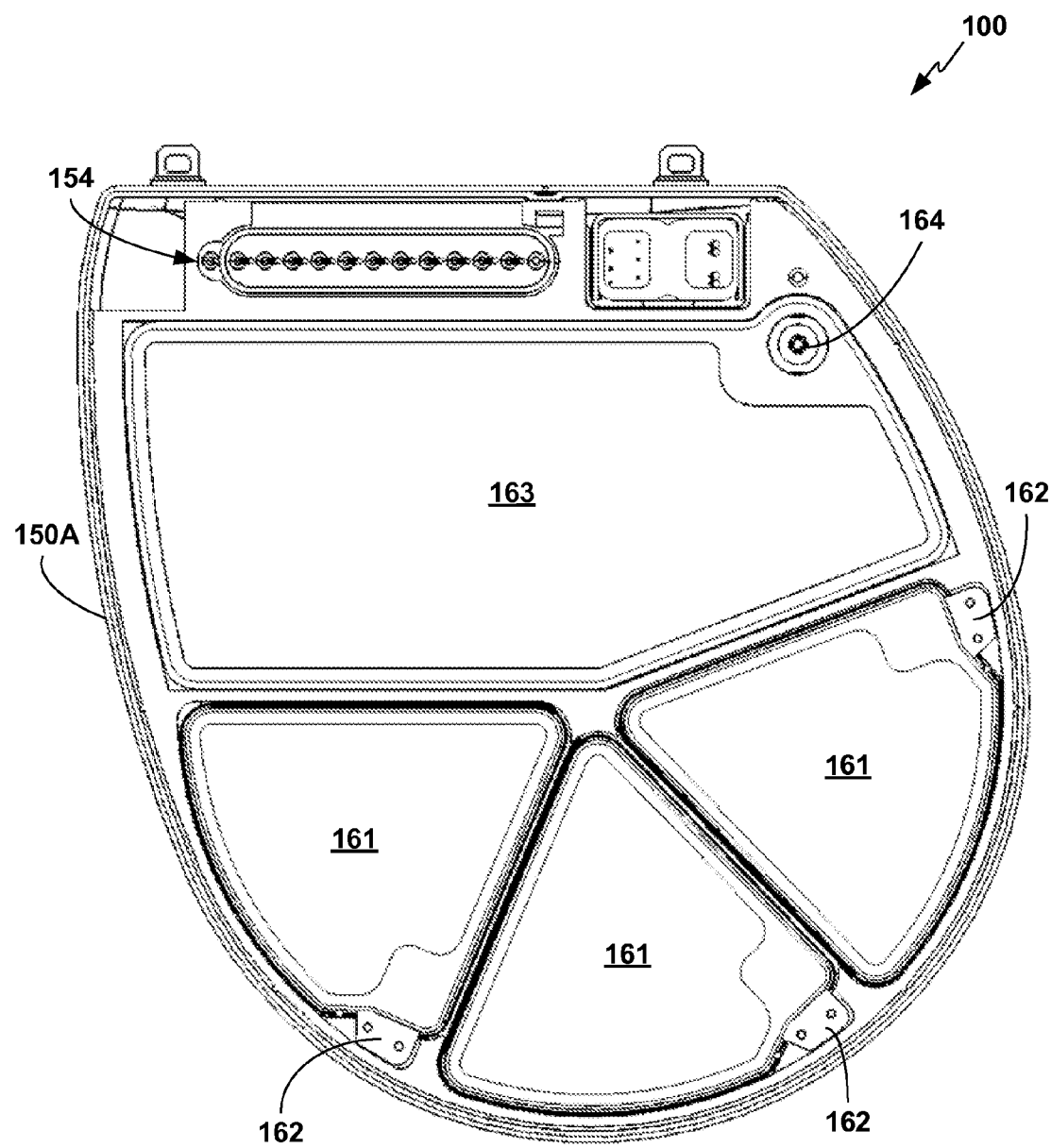
Figure 3C:
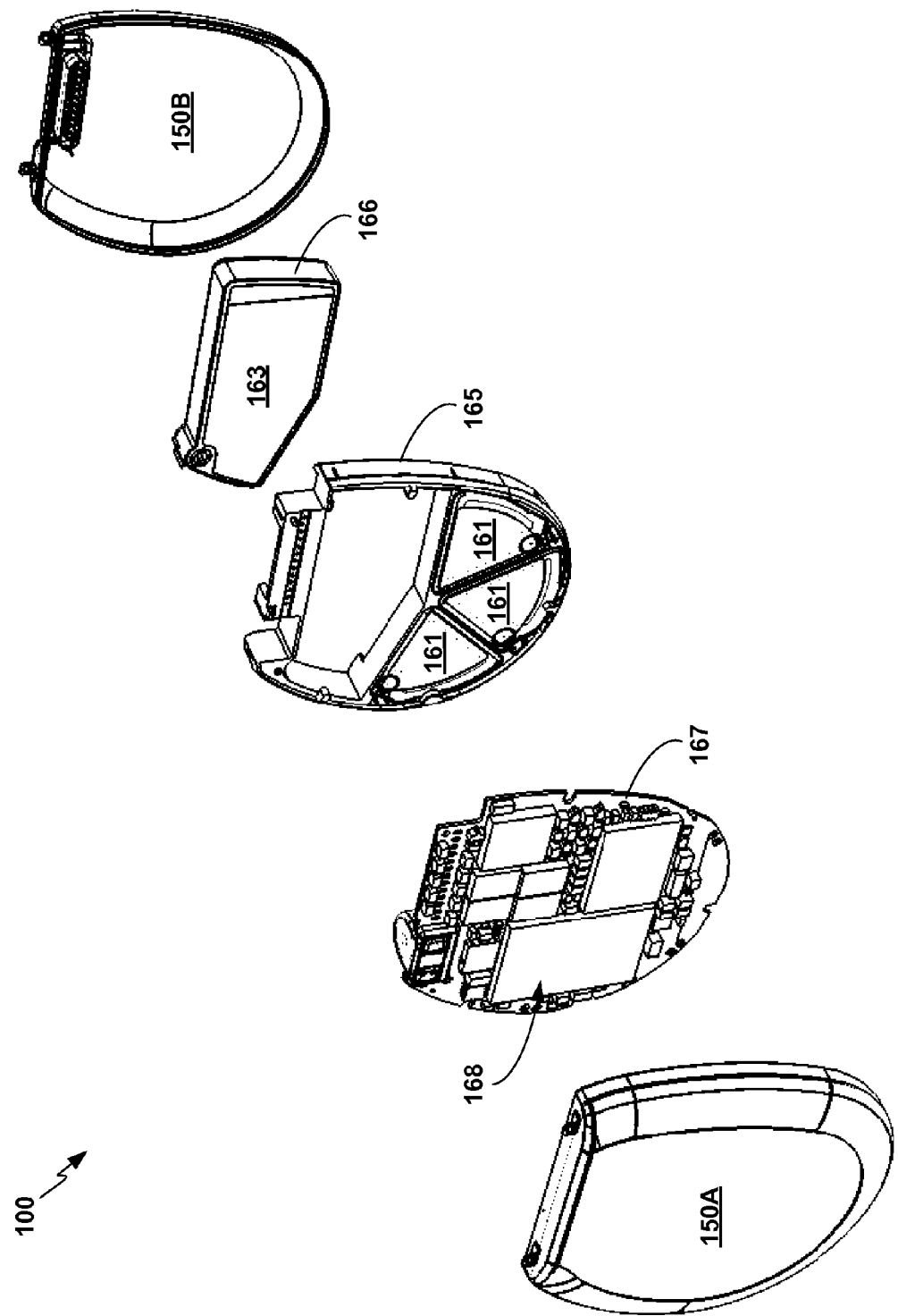
Figure 3D:
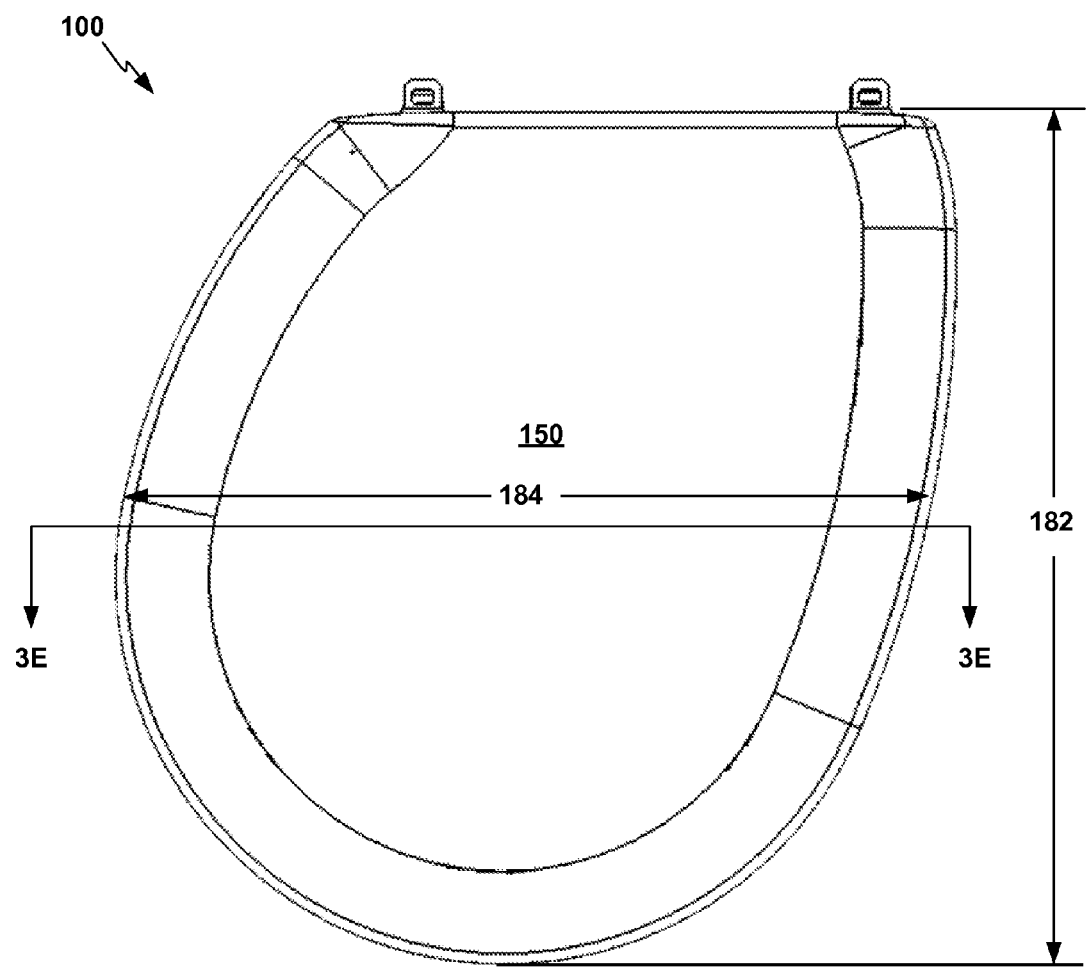
Figure 3E:
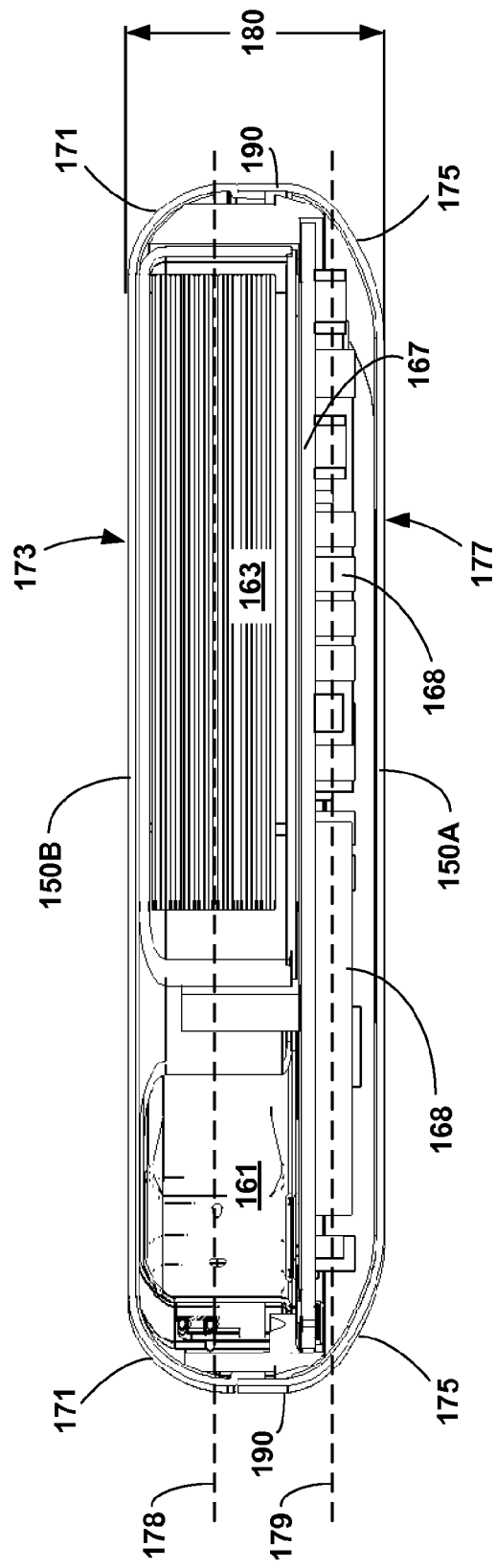

FIGS. 3A-3E illustrate an IMD 100. More specifically, FIG. 3A illustrates a perspective view of IMD 100, and FIG. 3B illustrates IMD 100 with housing portion 150B removed such that capacitors 161 and battery 163 are visible within housing portion 150A. In addition, FIG. 3C illustrates an exploded view of the components of IMD 100. FIG. 3D illustrates a side view of IMD 100 showing the profile of housing 150, and FIG. 3E illustrates a cross-section of IMD 100 as indicated on FIG. 3D.

As implanted within a patient, IMD 100 is suitable for delivering a medical therapy such as electrical stimulation therapy and/or sensing one or more physiological conditions of a patient. As an example, IMD 100 may provide some or all of the features described with respect to IMD 14. As indicated in FIG. 3A, IMD 100 includes housing 150 with feedthrough pins 154, which may connected to a medical lead connector assembly (not shown in FIGS. 3A-3E), such as medical lead connector assembly 40 (FIG. 2). The medical lead connector assembly may mount to housing 150 via brackets 152 and pins (not shown).

Housing 150 is formed from a biocompatible conductive material, such as a titanium alloy or stainless steel. For example, housing 150 may be formed from a first portion 150A and a second portion 150B, which may represent two mating clam shells in an overlapping or butt welded construction. Housing 150 may be hermetically sealed, e.g., by laser or resistance welding, to form an enclosure. Housing 150 encloses circuitry 167 (FIG. 3C) containing a therapy module configured to generate an electrical stimulation therapy and/or a sensing module to sense one or more physiological conditions for a patient, as well as a power supply and a telemetry module. Feedthroughs 154 extend through housing 150 and provide an electrical connection to the therapy module within housing 150.

Brackets 152 are secured to an exterior surface of housing 150. As an example, brackets 152 may be formed from the same or a similar biocompatible conductive material as housing 150 and welded to housing 150. As another example, brackets 152 may be molded as integral features of housing 150. Brackets 152 extend from housing 150 in a common direction toward lead connector assembly 110, the common direction being about perpendicular to the external surface of housing 150. Each of brackets 152 includes a hole for receiving a pin to mechanically secure a lead connector assembly to housing 150. Brackets 152 are positioned adjacent the four corners of an upper surface of housing 150.

As illustrated in FIG. 3B, IMD 100 includes a single battery 163 and three capacitors 161 along a common plane. To facilitate positioning each of capacitors 161 along the common plane, capacitors 161 are each sized to have a thickness corresponding to the thickness of the internal cavity of housing 150. Battery 163 may be a rechargeable or non-rechargeable battery and includes one or more electrochemical cells. A non-rechargeable battery may be selected to last for several years, while a rechargeable battery may be inductively charged from an external device, e.g., on a daily or weekly basis. Battery 163 is functional to supply power to circuitry 167 (FIG. 3C) of IMD 100 and may also be configured to charge capacitors 161. Battery 163 includes terminal 164, which is used to electrically connect battery 163 to circuitry 167 (FIG. 3C) of IMD 100. Battery 163 is shaped to fill the available space within the internal cavity of housing 150. For example, surface 166 (FIG. 3C) is curved so that is mates with the internal surface of housing 150.

Capacitors 161 are substantially similar to each other such that, each of capacitors 161 is physically and functionally interchangeable with each other. In this manner, only one capacitor design needs to be used in the production of IMD 100. As best illustrated in FIG. 3B, capacitors 161 each have a pie-shaped profile, which allows capacitors 161 to be efficiently positioned within the profile of IMD 100. Capacitors 161 are arranged to substantially fill a sector of a circle within the profile of housing 150. For example, the curved sides capacitors 161 mate with the internal surface of housing 150. Capacitors 161 also each include conductive tabs 162. Capacitors 161 are electrically connected capacitors 161 to circuitry 167 of IMD 100 via conductive tabs 162.

FIG. 3C illustrates the major components of IMD 100 in an exploded view. As shown in FIG. 3C, IMD 100 housing 150 is formed from a first portion 150A and a second portion 150B. First portion 150A and second portion 150B represent two mating clam shells in an overlapping or butt welded construction. In the example of IMD 100, both first portion 150A and second portion 150B conform to the profile of housing 150 (as best shown in FIG. 3D). First portion 150A and second portion 150B combine to form an internal cavity of housing 150.

FIG. 3D illustrates a side view of IMD 100 showing the profile of housing 150, and FIG. 3E illustrates a cross-section of IMD 100 as indicated on FIG. 3D. The profile of housing 150 provides height 182 and width 184. As one example, the height-to-width ratio of the profile of IMD 100 may be between about 1 to 1 and about 2 to 1. As another example, the height-to-width ratio of the profile of IMD 100 may be between about 1.5 to 1. Housing 150 further defines thickness 180, which is perpendicular to its profile. Thickness 180 is shorter than height 182 and width 184. As an example, thickness 180 maybe at least fifty percent shorter than height 182, and thickness 180 maybe at least fifty percent shorter than width 184. As referred to herein, the terms height, width and thickness are not intended to indicate any particular orientation for IMD 100.

As illustrated by the cross-section of IMD 100 in FIG. 3E, first portion 150A and second portion 150B of housing 150 forms opposing sides that extend in planes parallel to the height and the width of the housing. First portion 150A and second portion 150B of housing 150 include substantially flat surfaces 173, 177 towards the center of the profile of housing 150. Housing 150 also includes wall 190, which extends in a direction parallel to the thickness of the housing and about perpendicular to the height and the width of housing 150.

In addition, first portion 150A further forms a rounded outer edge 175 between wall 190 and flat surface 177. Rounded outer edge 175 encircles flat surface 177. Similarly, second portion 150B further forms a rounded outer edge 171 between wall 190 and flat surface 173. Rounded outer edge 171 encircles flat surface 173. As shown in FIG. 3E, flat surface 173 is larger than flat surface 177. In addition, rounded outer edge 175 has a larger radius of curvature than rounded outer edge 171. For example, the radius of curvature of rounded outer edge 175 may be at least double the radius of curvature of rounded outer edge 171. As shown in FIG. 3E, components 168 may be positioned away from wall 190 and towards the center of the profile of housing 150. Positioning components 168 away from wall 190 and towards the center of the profile of housing 150 facilitates a larger radius of curvature for rounded outer edge 175 without creating interference between circuitry 167 and housing 150.

The housing 150 is configured to be oriented within a patient such that flat surface 177 is located closer to the surface of the skin of the patient than flat surface 173. The larger curvature of rounded outer edge 175 mitigates stresses on the outer layers of patient tissue caused by the implantation of IMD 100 within a patient. For example, IMD 100 may be implanted such that flat surface 177 is adjacent the dermis, whereas flat surface 173 is adjacent muscular tissue. As another example, IMD 100 may be implanted such that flat surface 177 is adjacent muscular tissue, whereas flat surface 173 is closer to the patient's plural cavity.

IMD 100 further includes capacitors 161 and battery 163 within the internal cavity of housing 150. Capacitors 161 and battery 163 are positioned within a common plane 178 within the internal cavity of housing 150 and are constrained by support frame 165 such that capacitors 161 are adjacent to battery 163 within the internal cavity.

IMD 100 further includes circuitry 167 within the internal cavity of housing 150. Circuitry 167 may include a module configured to at least one of generate an electrical stimulation therapy for delivery to a patient or monitor a physiological parameter of the patient. As examples, circuitry 167 may include one or more elements previously described with respect to IMD 14 including processor 45, therapy module 46, sensing module 48, memory 49 and/or telemetry module 52. For example, the elements previously described with respect to IMD 14 may be individually or collectively embodied within one or more discrete components 168 of circuitry 167.

In one specific example, circuitry 167 may include a hybrid integrated circuit. Such a hybrid integrated circuit may be constructed of individual components 168, such as semiconductor devices (e.g. transistors and diodes) and passive components (e.g., resistors, inductors, transformers, and capacitors), bonded to a substrate or printed circuit board (PCB). In other examples, circuitry 167 may include a PCB with components 168 mounted directly to the PCB.

Circuitry 167 may also include a substrate with at least one ground plane. In one example, components 168 may be located on only a single side of the substrate and/or ground plane of circuitry 167 and opposite to battery 163 and capacitors 161 relative to the substrate and/or ground plane. In another example, components 168 may be located on two opposing sides of the substrate and/or ground plane of circuitry 167.

Circuitry 167 extends over both capacitors 161 and battery 163 within the internal cavity of housing 150 such that circuitry 167 is in a stacked arrangement relative to capacitors 161 and battery 163. For example, circuitry 167 is positioned along plane 178 (FIG. 3E), whereas capacitors 161 and battery 163 are positioned along plane 179 (FIG. 3E). Plane 179 is parallel to plane 178, but offset along the thickness 180 (FIG. 3E) of IMD 100. Both planes 178, 179 are about parallel to both of flat surfaces 173, 177.

As mentioned previously, in contrast to some previous IMD designs, circuitry 167 extends over both capacitors 161 and battery 163 instead of extending over only a battery. In addition capacitors 161 are positioned adjacent each other rather than being stacked about the thickness of IMD 100. The arrangement of capacitors 161 allows each capacitor 161 to have a greater thickness than if capacitors 161 were stacked about the thickness of IMD 100. The thickness of capacitors 161 may improve the volumetric efficiency of capacitors 161 as compared to thinner capacitors stacked about the thickness of IMD 100.

Figure 4:
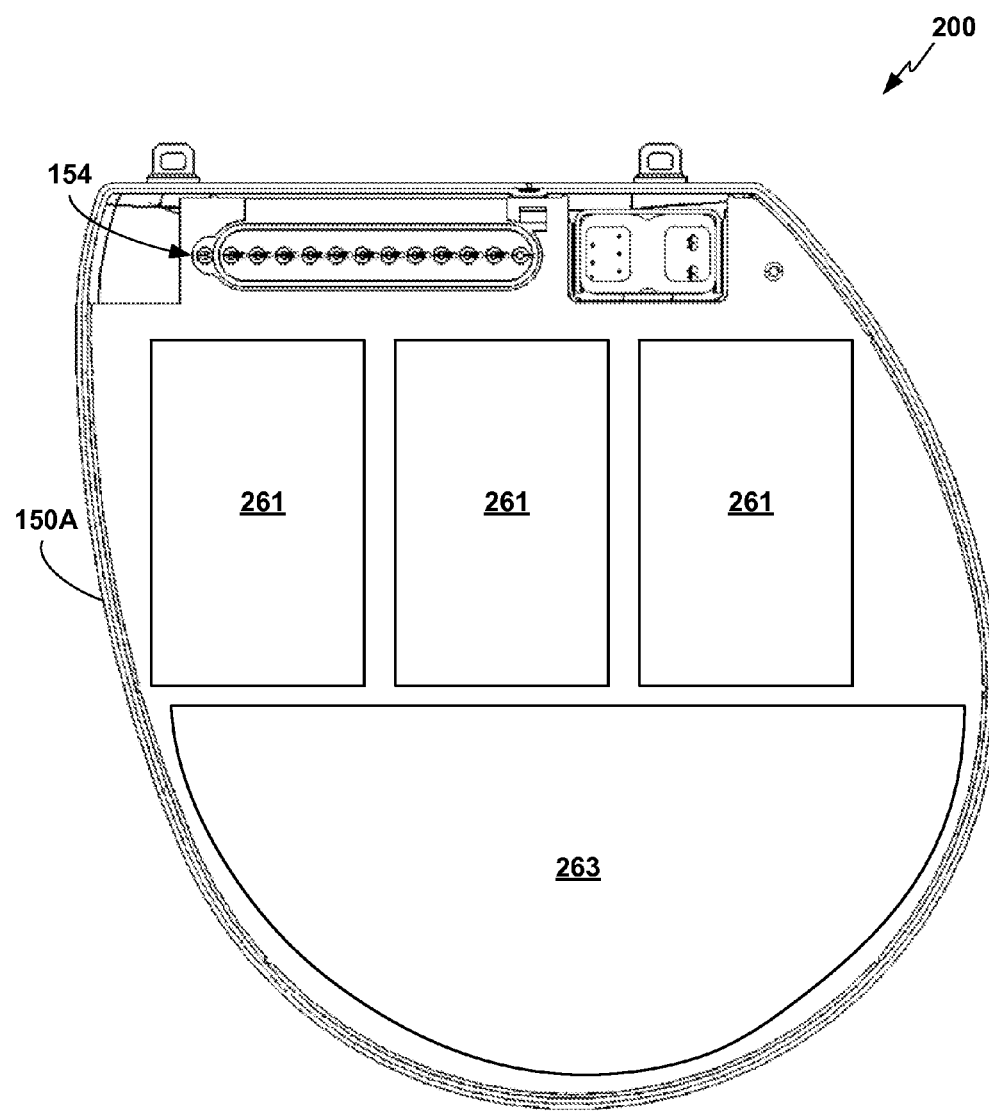
FIG. 4 illustrates a portion of an example IMD with circuitry that extends over both a battery and adjacent capacitors within an internal cavity of the IMD housing such that the circuitry is in a stacked arrangement relative to the battery and the capacitors, the illustrated portion including the battery and the capacitor.

FIG. 4 illustrates a portion of IMD 200. IMD 200 includes with circuitry that extends over both battery 263 and adjacent capacitors 261 within an internal cavity of the IMD housing such that the circuitry is in a stacked arrangement relative to battery 263 and capacitors 261. In FIG. 4, battery 263 and capacitors 261 are visible, but battery 263 and capacitors 261 obscure the circuitry that extends over both battery 263 and adjacent capacitors 261, similar to that illustrated with respect IMD 100 in FIG. 3B.

As implanted within a patient, IMD 200 is suitable for delivering a medical therapy such as electrical stimulation therapy and/or sensing one or more physiological conditions of a patient. Some aspects of IMD 200 are similar to aspects of IMD 100. For brevity, such aspects are described again with respect to IMD 200.

IMD 200 includes a single battery 263 and three capacitors 261 along a common plane. To facilitate positioning each of capacitors 261 along the common plane, capacitors 261 are each sized to have a thickness corresponding to the thickness of the internal cavity of the housing.

In contrast to capacitors 161 of IMD 100, capacitors 261 each have a rectangular-shaped profiles, although other capacitor profiles may also be used. Capacitors 261 are substantially similar to each other such that, each of capacitors 261 is physically and functionally interchangeable with each other. In this manner, only one capacitor design needs to be used in the production of IMD 200.

Battery 263 may be a rechargeable or non-rechargeable battery and includes one or more electrochemical cells. A non-rechargeable battery may be selected to last for several years, while a rechargeable battery may be inductively charged from an external device, e.g., on a daily or weekly basis. Battery 263 is functional to supply power to circuitry of IMD 200 and may also be configured to charge capacitors 261.

In contrast to some previous IMD designs, the circuitry of IMD 200 extends over both capacitors 261 and battery 263 instead of extending over only a battery. In addition capacitors 261 are positioned adjacent each other rather than being stacked about the thickness of IMD 200. The arrangement of capacitors 261 allows each capacitor 261 to have a greater thickness than if capacitors 261 were stacked about the thickness of IMD 200. The thickness of capacitors 261 may improve the volumetric efficiency of capacitors 261 as compared to thinner capacitors stacked about the thickness of IMD 200.

Figure 5:
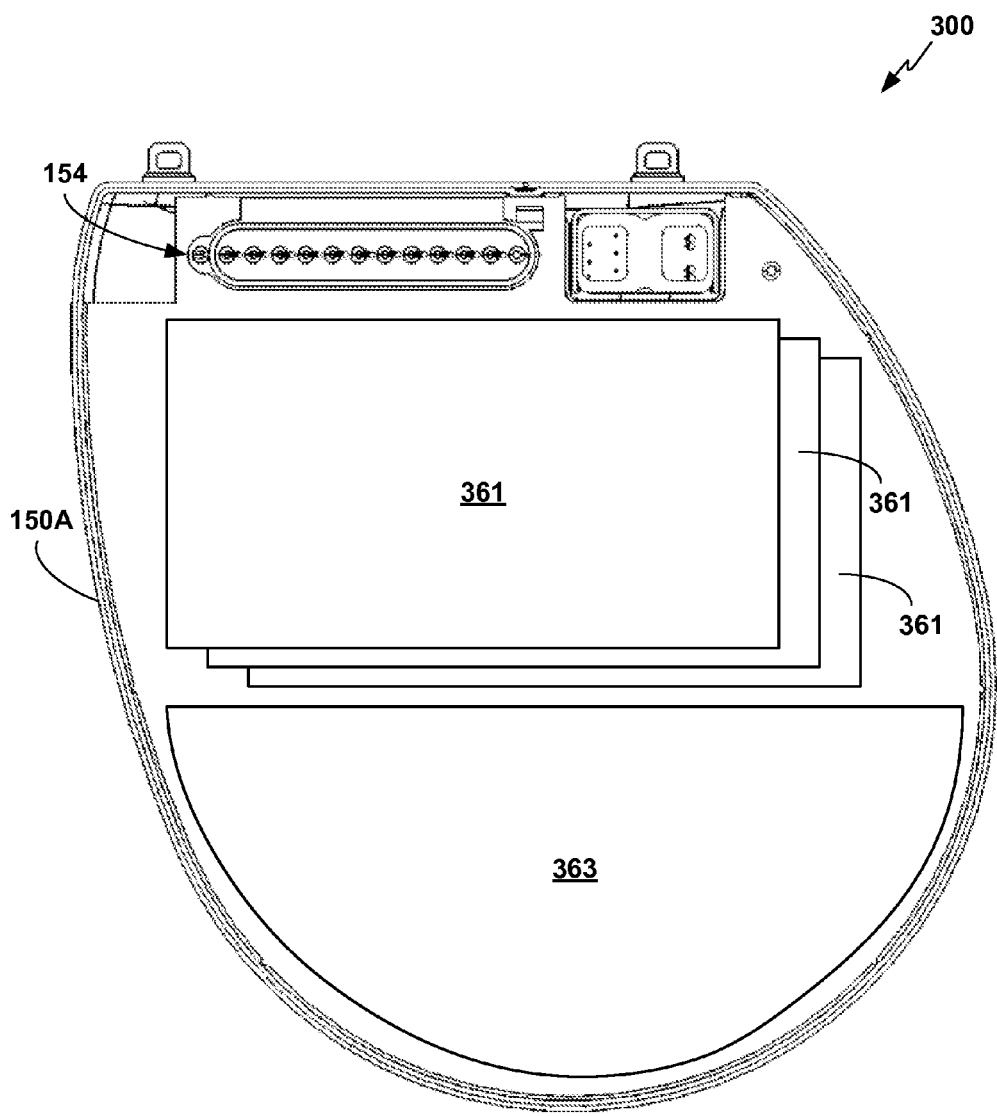
FIG. 5 illustrates a portion of an example IMD with circuitry that extends over both a battery and stacked capacitors within an internal cavity of the IMD housing such that the circuitry is in a stacked arrangement relative to the battery and the capacitors, the illustrated portion including the battery and the capacitors.

FIG. 5 illustrates a portion of IMD 300. IMD 300 includes with circuitry that extends over both battery 363 and adjacent capacitors 361 within an internal cavity of the IMD housing such that the circuitry is in a stacked arrangement relative to battery 363 and capacitors 361. In FIG. 4, battery 363 and capacitors 361 are visible, but battery 363 and capacitors 361 obscure the circuitry that extends over both battery 363 and adjacent capacitors 361, similar to that illustrated with respect IMD 100 in FIG. 3B. In contrast to some previous IMD designs, the circuitry of IMD 300 extends over both capacitors 361 and battery 363 instead of extending over only a battery.

As implanted within a patient, IMD 300 is suitable for delivering a medical therapy such as electrical stimulation therapy and/or sensing one or more physiological conditions of a patient. Some aspects of IMD 300 are similar to aspects of IMD 100. For brevity, such aspects are described again with respect to IMD 300.

IMD 300 includes a single battery 363 and a stack of three capacitors 361 along a common plane. To facilitate positioning each of capacitors 361 along the common plane, each of capacitors 361 is sized such that the stack of three capacitors 361 has a thickness corresponding to the thickness of the internal cavity of the housing.

In contrast to capacitors 161 of IMD 100, capacitors 361 each have a rectangular-shaped profiles, although other capacitor profiles may also be used. Capacitors 361 are substantially similar to each other such that, each of capacitors 361 is physically and functionally interchangeable with each other. In this manner, only one capacitor design needs to be used in the production of IMD 300.

Battery 363 may be a rechargeable or non-rechargeable battery and includes one or more electrochemical cells. A non-rechargeable battery may be selected to last for several years, while a rechargeable battery may be inductively charged from an external device, e.g., on a daily or weekly basis. Battery 363 is functional to supply power to circuitry of IMD 300 and may also be configured to charge capacitors 361.

The techniques described in this disclosure, including those attributed to IMD 14, programmer 24, IMD 100, IMD 200 and IMD 300 or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described herein. These and other examples are within the scope of the following claims.

What is claimed is:

1. An implantable medical device comprising:
a housing forming an internal cavity, the housing defining a profile with a height and a width and further defining a thickness perpendicular to its profile, wherein the thickness of the housing is shorter than both the height and the width of the profile of the housing;
at least one battery within the internal cavity;
at least one capacitor adjacent the battery within the internal cavity, the capacitor and the battery being located along the same plane within the internal cavity; and
hybrid integrated circuitry within the internal cavity, wherein the hybrid integrated circuitry comprises a module configured to at least one of generate an electrical stimulation therapy for delivery to a patient or monitor a physiological parameter of the patient, wherein the hybrid integrated circuitry comprises a processor mounted on the hybrid integrated circuit configured to control the module, and wherein the hybrid integrated circuitry extends over both the battery and the capacitor within the internal cavity such that the hybrid integrated circuitry is in a stacked arrangement along the thickness of the housing relative to the battery and the capacitor.

2. The implantable medical device of claim 1, further comprising:
electrical feedthroughs extending through the housing; and
a header assembly including one or more electrical connectors electrically coupled to the circuitry within the internal cavity via the feedthroughs.

3. The implantable medical device of claim 2, wherein the header assembly is a lead connector assembly.

4. The implantable medical device of claim 1, wherein components of the circuitry within internal cavity are located on only a single side of a substrate of the circuitry and opposite the battery and the capacitor relative to the substrate.

5. The implantable medical device of claim 1, wherein components of the circuitry within internal cavity are located on two opposing sides of a substrate of the circuitry.

6. The implantable medical device of claim 1, wherein the housing comprises:
a first portion with a clamshell shape that substantially conforms to the profile of components within the housing, the components including the battery, the capacitor and the circuitry; and
a second portion that combines with the first portion to form the internal cavity of the housing.

7. The implantable medical device of claim 1, wherein the housing forms opposing sides that extend in planes parallel to the height and the width of the housing, wherein the opposing sides include substantially flat surfaces towards the center of the profile of the housing.

8. The implantable medical device of claim 7, wherein the housing further forms a rounded outer edge at where at least one of the opposing sides meets a wall that extends in a direction parallel to the thickness of the housing.

9. The implantable medical device of claim 7, wherein the housing further forms:
a first rounded outer edge at where a first one of the opposing sides meets a wall that extends in a direction parallel to the thickness of the housing, wherein the first rounded edge encircles the first one of the opposing sides; and
a second rounded outer edge at where a second one of the opposing sides meets the wall that extends in the direction parallel to the thickness of the housing, wherein the second rounded edge encircles the second one of the opposing sides, wherein a radius of curvature for the first rounded edge is at least double a radius of curvature for the second rounded edge.

10. The implantable medical device of claim 1, wherein the at least one capacitor includes two or more substantially similar capacitors, the substantially similar capacitors being physically and functionally interchangeable with each other.

11. The implantable medical device of claim 1, wherein the at least one capacitor includes two or more capacitors, each of the capacitors being located along the plane with the battery.

12. The implantable medical device of claim 1,
wherein the at least one capacitor includes three substantially similar capacitors, the substantially similar capacitors being physically and functionally interchangeable with each other,
wherein each of the substantially similar capacitors are located along the plane with the battery,
wherein each of the substantially similar capacitors defines a pie-shaped profile, and
wherein the capacitors are arranged to substantially fill a sector of a circle within the profile of housing.

13. The implantable medical device of claim 12, wherein the implantable medical device includes exactly one battery comprising electrochemical cells.

14. The implantable medical device of claim 1,
wherein the at least one capacitor includes three substantially similar capacitors, the substantially similar capacitors being physically and functionally interchangeable with each other,
wherein each of the substantially similar capacitors are arranged to form a stack of capacitors,
wherein the stack of capacitors is located along the plane with the battery.

15. The implantable medical device of claim 1,
wherein the at least one capacitor includes two or more substantially similar capacitors, the substantially similar capacitors being physically and functionally interchangeable with each other,
wherein each of the substantially similar capacitors are located along the plane with the battery,
wherein each of the substantially similar capacitors defines a rectangular-shaped profile.

16. A system comprising:
an implantable medical device comprising:
  a housing forming an internal cavity, the housing defining a profile with a height and a width and further defining a thickness perpendicular to its profile, wherein the thickness of the housing is shorter than both the height and the width of the profile of the housing,
  at least one battery within the internal cavity,
  at least one capacitor adjacent the battery within the internal cavity, the capacitor and the battery being located along the same plane within the internal cavity;
  hybrid integrated circuitry within the internal cavity, wherein the hybrid integrated circuitry comprises a module configured to at least one of generate an electrical stimulation therapy for delivery to a patient or monitor a signal indicative of a physiological parameter of the patient, wherein the hybrid integrated circuitry comprises a processor mounted on the hybrid integrated configured to control the module, wherein the hybrid integrated circuitry extends over both the battery and the capacitor within the internal cavity such that the hybrid integrated circuitry is in a stacked arrangement along the thickness of the housing relative to the battery and the capacitor, and
  a header assembly external to the housing, the header assembly being in electrical contact with the hybrid integrated circuitry within the internal cavity; and
at least one medical lead in mechanical and electrical contact with the implantable medical device via the header assembly.

17. The system of claim 16 further comprising a programmer configured to facilitate user interaction with the implantable medical device to retrieve physiological or diagnostic information from the implantable medical device when the implantable medical device is implanted within a patient.

* * * * *